(12) United States Patent
Stenzler

(10) Patent No.: US 11,672,441 B2
(45) Date of Patent: Jun. 13, 2023

(54) LOW FLOW SPIROMETER TURBINE

(71) Applicant: MONITORED THERAPEUTICS, INC., Dublin, OH (US)

(72) Inventor: Alex Stenzler, Long Beach, CA (US)

(73) Assignee: Monitored Therapeutics, inc., Dublin, OH (US)

( * ) Notice: Subject to any disclaimer, the term of this patent is extended or adjusted under 35 U.S.C. 154(b) by 244 days.

(21) Appl. No.: 17/119,322

(22) Filed: Dec. 11, 2020

(65) Prior Publication Data
US 2021/0093225 A1 Apr. 1, 2021

Related U.S. Application Data

(63) Continuation of application No. 16/671,027, filed on Oct. 31, 2019, now Pat. No. 10,939,849.

(60) Provisional application No. 62/753,172, filed on Oct. 31, 2018.

(51) Int. Cl.
*A61B 5/09* (2006.01)
*F01D 5/14* (2006.01)
*F01D 5/28* (2006.01)

(52) U.S. Cl.
CPC .............. *A61B 5/09* (2013.01); *F01D 5/141* (2013.01); *F01D 5/28* (2013.01)

(58) Field of Classification Search
None
See application file for complete search history.

(56) References Cited

U.S. PATENT DOCUMENTS

| | | | | |
|---|---|---|---|---|
| 5,003,828 A | * | 4/1991 | van den Burg | G01F 1/103 73/861.89 |
| 7,794,206 B2 | * | 9/2010 | Keber | F04D 29/281 416/189 |
| 2002/0096197 A1 | * | 7/2002 | Ackerman | F02C 7/30 134/22.18 |
| 2008/0149141 A1 | * | 6/2008 | Sales | F01D 25/002 134/198 |
| 2015/0119744 A1 | * | 4/2015 | Lawson | G01F 15/04 600/539 |
| 2017/0270260 A1 | * | 9/2017 | Shetty | G16H 40/67 |

* cited by examiner

*Primary Examiner* — Harshad R Patel
(74) *Attorney, Agent, or Firm* — Riverside Law LLP

(57) ABSTRACT

A spirometer turbine assembly is described, having a housing with a proximal end opening, a distal end opening and an airflow channel therebetween. A first flow director has a first plurality of flow director blades with distal edges that curve in a plane perpendicular to a longitudinal axis of the airflow channel, and a vane is connected to an axel positioned distal to the first flow director. A spirometer turbine assembly having an anti-static material is also described.

14 Claims, 4 Drawing Sheets

| Turbine | Terminal Flow Rate |
|---|---|
| MIR | 0.044 L/s (2.64 L/m) |
| ERT AM-3 | 0.053 L/s (3.20 L/m) |
| Curved Blade | 0.015 L/s (0.92 L/m) |

FIG. 4

LOW FLOW SPIROMETER TURBINE

CROSS-REFERENCE TO RELATED APPLICATIONS

This application is a continuation of U.S. application Ser. No. 16/671,027, filed Oct. 31, 2019, which claims priority to U.S. provisional application No. 62/753,172 filed on Oct. 31, 2018 and incorporated herein by reference in its entirety.

BACKGROUND OF THE INVENTION

Spirometry is a common and well established pulmonary function test for evaluating patients with conditions such as asthma, cystic fibrosis, pulmonary fibrosis and COPD. The testing assesses function of the patient's lungs by measuring the volume and flow of air that a patient is able to inhale and exhale.

Turbine spirometers generally include a mouth piece for the user to blow on connected to a flow director, which causes exhaled air to swirl, twisting the air into a vortex. The angular velocity of the vortex is proportional to the flow rate of air passing through the mouth piece. A vane beyond the flow director is typically a flat rectangular piece of plastic film mounted on an axle. The exhaled swirled air applies a torque to the vane which rotates at the same angular velocity as the vortex. The angular velocity of the vane is therefore proportional to the flow of air within the tube. A light source, such as an infrared transmitter, transmits a continuous infrared beam that is interrupted by the vane as it rotates, resulting in infrared pulses. An infrared receiver receives the infrared pulses and a controller processes the received infrared pulses to determine the volume and flow rate of the air exhaled by the subject. Depending on the type of spirometer, it may include two flow directors, one at each end of the turbine assembly housing on opposite sides of the vane, which means that it can be used to test both inhalation and exhalation.

To be effective, spirometers should be able to perform at very low flow rates so that valuable patient data is not missed. In fact, the American Thoracic Society/European Respiratory Society (ATS/ERS) "Standardization of Spirometry" states that "The level of minimum detectable flow should be 0.025 L/s" (1.5 L/m). This is important for accurate measurement of forced vital capacity (FVC). However, when spirometers are tested to the ATS waveforms, they don't specifically test at flow levels that low. Therefore, many spirometers that pass the ATS waveforms and are FDA cleared for sale don't actually meet all of the ATS/ERS standard. Turbine spirometers are reported to have the greatest difficulty meeting this low flow requirement.

There are various issues that lead to poor low flow rate performance in conventional turbine spirometers that have not been previously recognized in the prior art. One issue is the static discharge caused by the edge alignment between the inside edge of flow director blades and the outside edge of the vane, as shown in the spirometer 10 of prior art FIG. 1. Flow director blades 12 in conventional spirometers 10 are pitched or scooped for initiating a vortical airflow (see offset leading 14 and trailing 16 edges), however the profile of each flow director blade 12 in the plane perpendicular to the longitudinal axis remains straight, just like the edge of the adjacent vane 20 (see also for example Edwards et al., U.S. Pat. No. 6,126,613, and Meng et al. U.S. Pub. No. 2012/0029376). This results in static electricity of the flow director blade 12 being exerted on the entire edge of the vane 20 as they align, which builds resistance and affects the ability of the vane 20 to spin freely and measure low flows. When the exhalation flow rate reaches very low flows, this static charge can cause the vane to completely stop spinning before airflow stops.

Another issue that leads to poor low flow rate performance in conventional turbine spirometers is the "dead band" effect. Conventional turbine spirometers have spaces 18 between the flow director blades as shown in prior art FIG. 1. During low flow rates, the separation between flow director blades creates "dead bands", which allows air to flow through linearly without engaging a flow director blade edge, and thus without redirection. "Dead bands" enable the vane to prematurely stop in those spaces since sufficient torque cannot be applied to the blade within that space.

Thus, what is needed in the art is a spirometer turbine assembly that can function effectively at very low flow rates so that critical patient data is not missed, and is not prone to the static discharge and "dead band" effects previously unrecognized in the prior art.

SUMMARY OF THE INVENTION

In one embodiment, a spirometer turbine assembly includes a housing having a proximal end opening, a distal end opening and an airflow channel therebetween, a first flow director having a first plurality of flow director blades with distal edges that curve in a plane perpendicular to a longitudinal axis of the airflow channel, and a vane connected to an axel positioned distal to the first flow director. In one embodiment, an edge of each of the first plurality of flow director blades connects to an edge of an adjacent flow director blade. In one embodiment, a vane edge and blade edges of the flow director continuously overlap at one or more points as the vane spins. In one embodiment, the first flow director includes an odd number of flow director blades. In one embodiment, the first flow director blades comprise an anti-static material. In one embodiment, the anti-static material is an anti-static coating. In one embodiment, the anti-static material is an anti-static plastic composition. In one embodiment, the spirometer turbine assembly includes a second flow director having a second plurality of flow director blades with proximal edges that curve in a plane perpendicular to the longitudinal axis, the second flow director positioned distal of the vane. In one embodiment, an edge of each of the second plurality of flow director blades connects to an edge of an adjacent flow director blade. In one embodiment, second flow director comprises an odd number of flow director blades. In one embodiment, the spirometer turbine assembly is configured to maintain the vane spinning at flow rates between 0.015 L/s and 0.025 L/s. In one embodiment, the spirometer turbine assembly is configured to maintain the vane spinning at flow rates between 0.015 L/s and 0.020 L/s. In one embodiment, the spirometer turbine assembly is configured to maintain the vane spinning at flow rates of 0.015 L/s. In one embodiment, the spirometer turbine assembly is configured to be oriented vertically during use.

In one embodiment, a spirometer turbine assembly includes a housing having a proximal end opening, a distal end opening and an airflow channel therebetween, a first flow director having a first plurality of flow director blades, and a vane connected to an axel positioned distal to the first flow director, wherein at least one of the flow director and vane comprise an anti-static material. In one embodiment, the anti-static material is an anti-static coating. In one embodiment, the anti-static material is an anti-static plastic composition. In one embodiment, the flow director blades comprise distal edges that curve in a plane perpendicular to a longitudinal axis of the airflow channel. In one embodiment, an edge of each of the first plurality of flow director blades connects to an edge of an adjacent flow director blade. In one embodiment, a vane edge and blade edges of the flow director continuously overlap at one or more points as the vane spins.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which:

FIG. 4 is a table of terminal flow rate results for an experimental setup testing flow rates of conventional spirometer turbines and an improved spirometer turbine assembly according to embodiments described herein.

DETAILED DESCRIPTION OF THE INVENTION

Figure 1:
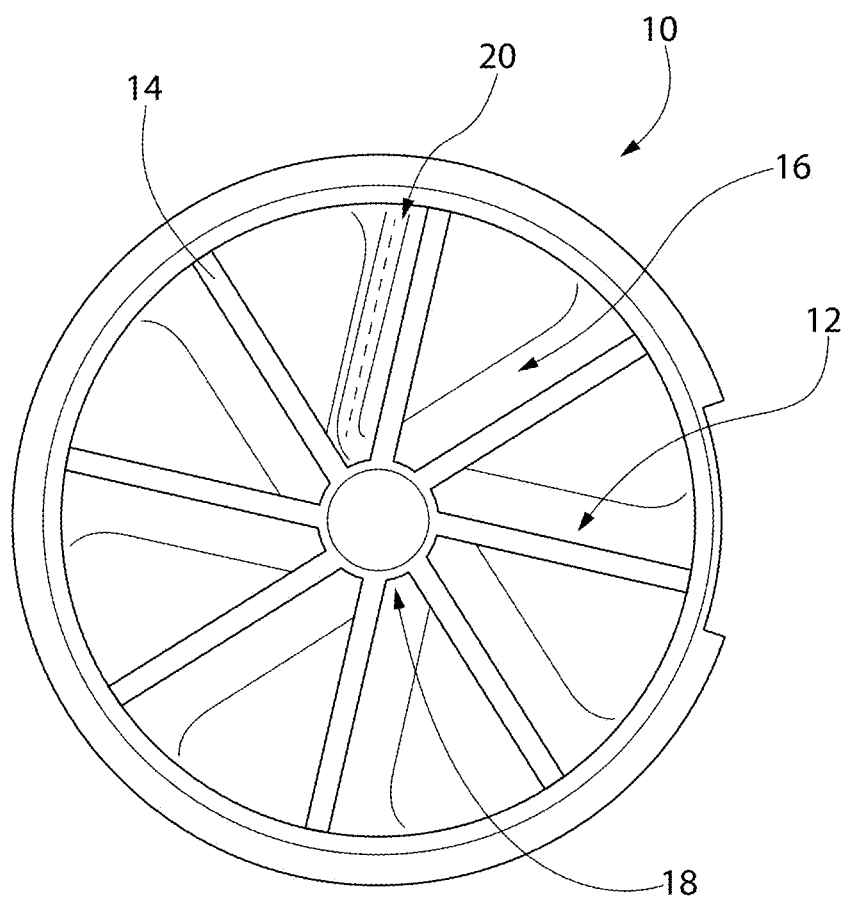
FIG. 1 is top-down view of a prior art spirometer turbine assembly.

It is to be understood that the figures and descriptions of the present invention have been simplified to illustrate elements that are relevant for a more clear comprehension of the present invention, while eliminating, for the purpose of clarity, many other elements found in systems and methods of spirometry. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Ranges: throughout this disclosure, various aspects of the invention can be presented in a range format. It should be understood that the description in range format is merely for convenience and brevity and should not be construed as an inflexible limitation on the scope of the invention. Where appropriate, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Referring now in detail to the drawings, in which like reference numerals indicate like parts or elements throughout the several views, in various embodiments, presented herein is a spirometer turbine assembly.

Embodiments of spirometer turbine assemblies described herein include flow director blades that are curved so that they don't align with straight vane edges, which minimizes the buildup of static electricity resistance. Generation of static electricity between these two components of the turbine is minimized, and the vane can continue to spin freely without static electricity lockup at very low flows, continuing to measure critical patient data. Anti-static materials can also be incorporated into the flow director and vane to promote turbine assembly function at low flows. Further, flow director blades have connected edges, resulting in a zero-gap between blades about the hub. This way, no matter what position the vane is in, it will always lie in the path of air flow right off some point on the edge of a blade, and "dead bands" are eliminated.

Figure 2A:
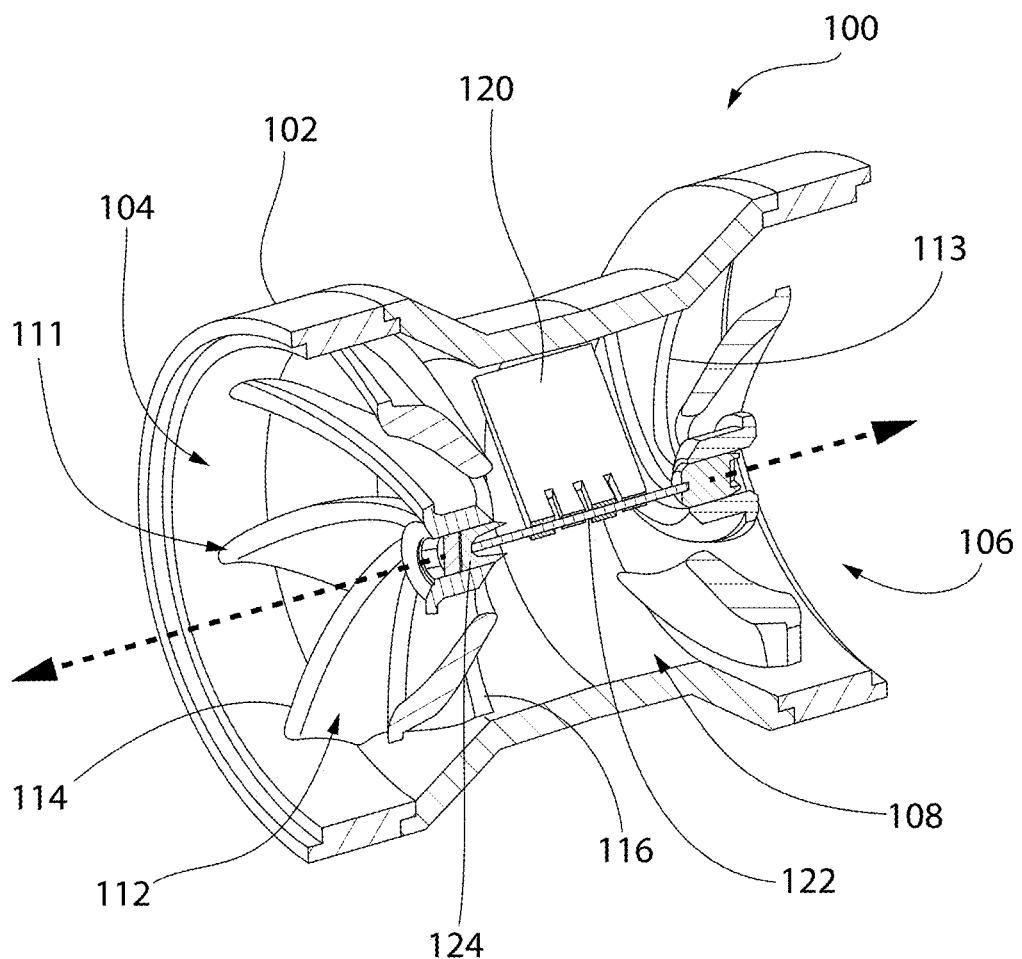
FIG. 2A is a partial cutaway perspective view of a spirometer turbine assembly according to one embodiment.
Figure 2B:
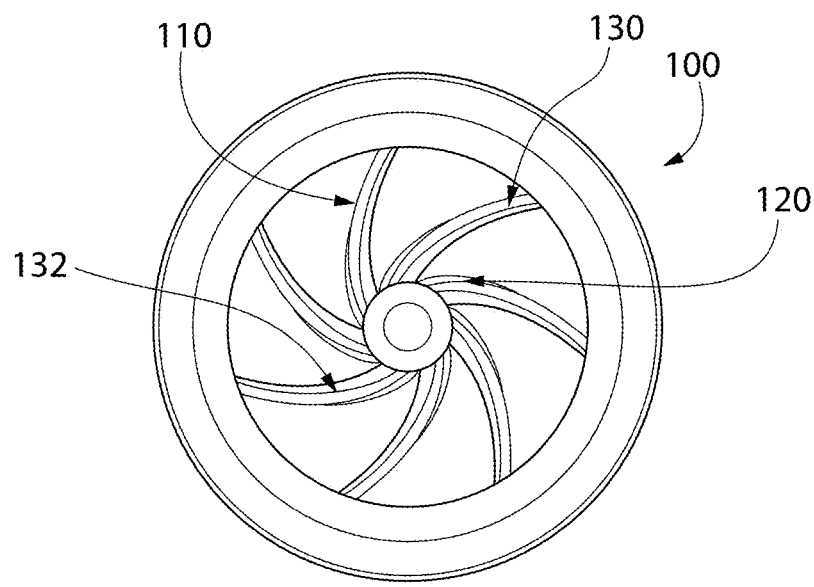
FIG. 2B is a top-down view of the spirometer turbine assembly according to one embodiment.

In one embodiment, with reference now to FIGS. 2A and 2B, a spirometer turbine assembly 100 includes a breathing tube housing 102 having a proximal end opening 104, a distal end opening 106 and an airflow channel 108 therebetween. The proximal end opening 104 can connect to a mouthpiece that the patient exhales and inhales on. A first flow director 111 is positioned at the proximal opening 104 for directing exhaled air and generating a vortical airflow. The first flow director 111 has multiple flow director blades 112 with leading proximal 114 and trailing distal 116 edges. The distal edges 116 curve in a plane perpendicular to a longitudinal axis of the airflow channel 108 (perpendicular plane depicted in FIG. 2B). A vane 120 connected to an axel 122 having a jeweled bearing 124 is positioned distal to the first flow director 111. A second flow director 113 can be positioned distal of the vane 120 for generating a vortical flow during inhalation.

As illustrated specifically in FIG. 2*b*, the outside edge of the vane 120 does not align with the inside edge of flow director blades 110, which minimizes the buildup of static electricity resistance. Since the alignment of the outside edge and the vane 120 is only ever at a small point 130, 132, generation of static electricity between these two components of the turbine is minimized, and the vane 120 can continue to spin freely without static electricity lockup at very low flows, continuing to measure critical patient data.

Figure 3:
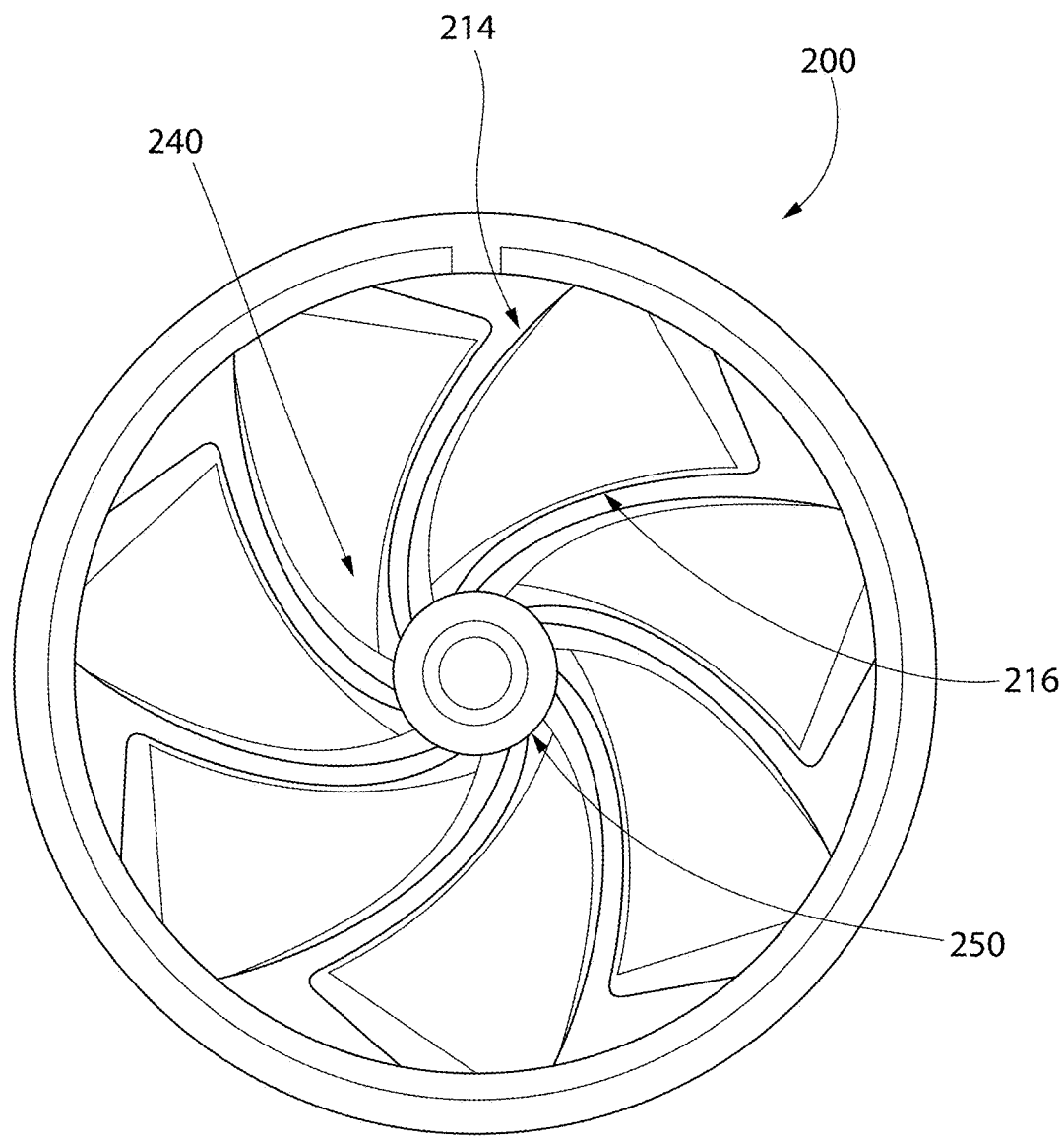
FIG. 3 is a top-down view of a spirometer turbine assembly according to one embodiment.

With reference now to FIG. 3, in one embodiment, a spirometer turbine assembly flow director 200 can have leading edges 214 that overlap or connect with trailing edges 216 edges of adjacent blades, resulting in a zero-gap 240 between blades about the hub 250. Advantageously, no matter what position the vane is in, it will always lie in the path of air flow right off some point on the edge of a blade, and "dead bands" are eliminated. In one embodiment, having an odd number of blades eliminates symmetry and also places at least one point of the vane always at the leading edge of a blade. In one embodiment, the vane edge and flow director blade edges are configured so that they continuously overlap at one or more points as the vane spins.

Anti-static materials can also be incorporated into the flow director and vane to promote turbine assembly function at low flows. In one embodiment, flow director blades include an anti-static material. In one embodiment, the anti-static material is an anti-static coating or skin. In one embodiment, the anti-static material is an anti-static plastic composition. In one embodiment, anti-static additives are added to the components during manufacturing. In one embodiment, an anti-static spray coating is applied to the components including a polymer and a solvent made from deionized water and alcohol. In one embodiment, a highly conductive element such as a copper wire is incorporated into the turbine assembly to dissipate static buildup.

Embodiments described herein allow vane turbines to keep spinning in response to very low flow. Additional features to overcome the drag of the spindle in the bearing can include a vertical turbine that reduces drag caused by the spindle bearing, such as the vertical turbine described in Lawson et al., International Pub. No. WO 2013/150267, which describes a swan neck-shaped or elbow-shaped mouth piece used with a turbine spirometer to convert it into a spirometer in which the angle of air entry is diverted in the mouth piece such that it impacts the vane of the spirometer at an inclined angle. Compared to lung function turbines that are oriented horizontally during use and have increased drag on the lateral sides of the bearings, orienting the turbine assembly so that the vane rotates about a vertical axis further promotes improved vane rotation under low flow rates.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Flow rate tests were performed on two conventional FDA approved turbines (models MIR and ERT AM-3) and one curved blade turbine having a flow director with curved and zero-gap blade edges. Using a low flow blower and a calibrated TSI electronic flow meter to measure the actual flow, the turbine vanes eventually stopped spinning as the flow is slowly decreased, and the terminal flow rate was recorded.

Results:

Terminal flow rate results are shown in FIG. 4. The MIR turbine stopped measuring flow at 0.044 L/s. The ERT AM-3 turbine stopped measuring flow at 0.053 L/s. The improved turbine with curved blades stopped measuring flow at 0.015 L/s. Anti-static materials such as additives or coating were not implemented into the device used in the experiment, but can be utilized to achieve even lower functional flow rates.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention.

What is claimed is:

1. A spirometer turbine assembly comprising:
    a housing having a proximal end opening, a distal end opening and an airflow channel therebetween;
    a first flow director having a first plurality of flow director blades; and
    a vane connected to an axel positioned distal to the first flow director;
    wherein at least one of the flow director and vane comprise an anti-static material;
    wherein the spirometer turbine assembly is configured to be oriented vertically during use; and
    wherein a vane edge and blade edges of the flow director continuously overlap at one or more points as the vane spins for minimizing buildup of static electricity resistance at low flows.

2. The spirometer turbine assembly of claim 1, wherein the first flow director comprises an odd number of flow director blades.

3. The spirometer turbine assembly of claim 1, wherein the anti-static material is an anti-static plastic composition.

4. The spirometer turbine assembly of claim 1, wherein the spirometer turbine assembly is configured to maintain the vane spinning at flow rates between 0.015 L/s and 0.025 L/s.

5. The spirometer turbine assembly of claim 1, wherein the spirometer turbine assembly is configured to maintain the vane spinning at flow rates between 0.015 L/s and 0.020 L/s.

6. The spirometer turbine assembly of claim 1, wherein the spirometer turbine assembly is configured to maintain the vane spinning at flow rates of 0.015 L/s.

7. The spirometer turbine assembly of claim 1, wherein the anti-static material is an anti-static coating.

8. A spirometer turbine assembly for low flow operation comprising:
    a housing having a proximal end opening, a distal end opening and an airflow channel therebetween;
    a first flow director having a first plurality of flow director blades; and
    a vane connected to an axel positioned distal to the first flow director;
    wherein at least one of the flow director and vane comprise an anti-static material;
    wherein the spirometer turbine assembly is configured to be oriented vertically during use; and
    wherein the first flow director comprises an odd number of flow director blades for minimizing buildup of static electricity resistance at low flows.

9. The spirometer turbine assembly of claim 8, wherein a vane edge and blade edges of the flow director continuously overlap at one or more points as the vane spins.

10. The spirometer turbine assembly of claim 8, wherein the anti-static material is an anti-static plastic composition.

11. The spirometer turbine assembly of claim 8, wherein the spirometer turbine assembly is configured to maintain the vane spinning at flow rates between 0.015 L/s and 0.025 L/s.

12. The spirometer turbine assembly of claim 8, wherein the spirometer turbine assembly is configured to maintain the vane spinning at flow rates between 0.015 L/s and 0.020 L/s.

13. The spirometer turbine assembly of claim 8, wherein the spirometer turbine assembly is configured to maintain the vane spinning at flow rates of 0.015 L/s.

14. The spirometer turbine assembly of claim 8, wherein the anti-static material is an anti-static coating.

* * * * *